United States Patent
Lavoritano et al.

(10) Patent No.: US 11,457,950 B2
(45) Date of Patent: Oct. 4, 2022

(54) LOCKING SYSTEM AND METHOD

(71) Applicant: DePuy Synthes Products, Inc., Raynham, MA (US)

(72) Inventors: Scott Lavoritano, West Chester, PA (US); Brent Oberholtzer, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 20 days.

(21) Appl. No.: 16/859,166

(22) Filed: Apr. 27, 2020

(65) Prior Publication Data

US 2021/0330357 A1    Oct. 28, 2021

(51) Int. Cl.
*A61B 17/62* (2006.01)

(52) U.S. Cl.
CPC ..................... *A61B 17/62* (2013.01)

(58) Field of Classification Search
CPC .............................................. A61B 17/60–666
See application file for complete search history.

(56) References Cited

U.S. PATENT DOCUMENTS

| | | | | |
|---|---|---|---|---|
| 4,308,863 A | * | 1/1982 | Fischer ................. | A61B 17/62 606/56 |
| 4,450,834 A | * | 5/1984 | Fischer ................. | A61B 17/62 606/102 |
| 5,290,308 A | * | 3/1994 | Knight .................. | A61B 17/29 604/247 |
| 5,484,437 A | * | 1/1996 | Michelson ............. | A61F 2/446 606/86 A |
| 6,030,386 A | * | 2/2000 | Taylor .................. | A61B 17/62 606/54 |
| 8,506,566 B2 | | 8/2013 | Karidis et al. | |
| 8,864,763 B2 | | 10/2014 | Murray et al. | |
| 9,381,042 B2 | | 7/2016 | Ross et al. | |
| 10,080,586 B2 | | 9/2018 | Ross et al. | |
| 10,376,285 B2 | | 8/2019 | Singh et al. | |
| 10,405,888 B2 | | 9/2019 | Singh et al. | |
| 2011/0208187 A1 | * | 8/2011 | Wong ................. | A61B 17/6416 606/59 |
| 2014/0276817 A1 | * | 9/2014 | Murray ................ | A61B 17/62 606/56 |
| 2014/0276822 A1 | * | 9/2014 | Cresina ............... | A61B 17/66 606/57 |

(Continued)

FOREIGN PATENT DOCUMENTS

| | | |
|---|---|---|
| CN | 109077786 A | 12/2018 |
| WO | 2019/232939 A1 | 12/2019 |

*Primary Examiner* — Nicholas J Plionis
(74) *Attorney, Agent, or Firm* — BakerHostetler

(57) ABSTRACT

An strut assembly extends along a strut axis and comprises a strut body, an actuator, and a locking assembly. The strut body includes a rod and a sleeve. The rod is translatable relative to the sleeve along the strut axis. The actuator is linearly engaged with the sleeve such that linear movement of the actuator causes linear movement of the sleeve. The locking assembly includes a lock member configured to transition between a locked position in which the lock member engages both the sleeve and the actuator such that rotation between the sleeve and the actuator is substantially prevented, and an unlocked position in which the lock member is spaced apart from the sleeve such that the actuator is substantially free to rotate about the sleeve.

14 Claims, 10 Drawing Sheets

(56) References Cited

U.S. PATENT DOCUMENTS

2016/0022314 A1* 1/2016 Bordeaux .............. A61B 17/60
  606/56
2017/0042580 A1* 2/2017 Mannanal .......... A61B 17/8894
2018/0368887 A1* 12/2018 Lauf ...................... A61B 17/62
2021/0000508 A1* 1/2021 Sun ........................ A61B 90/39

* cited by examiner

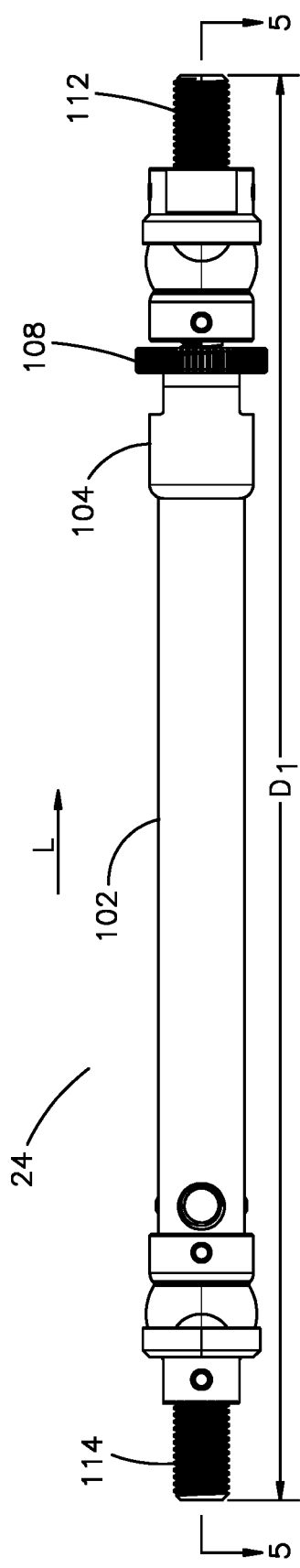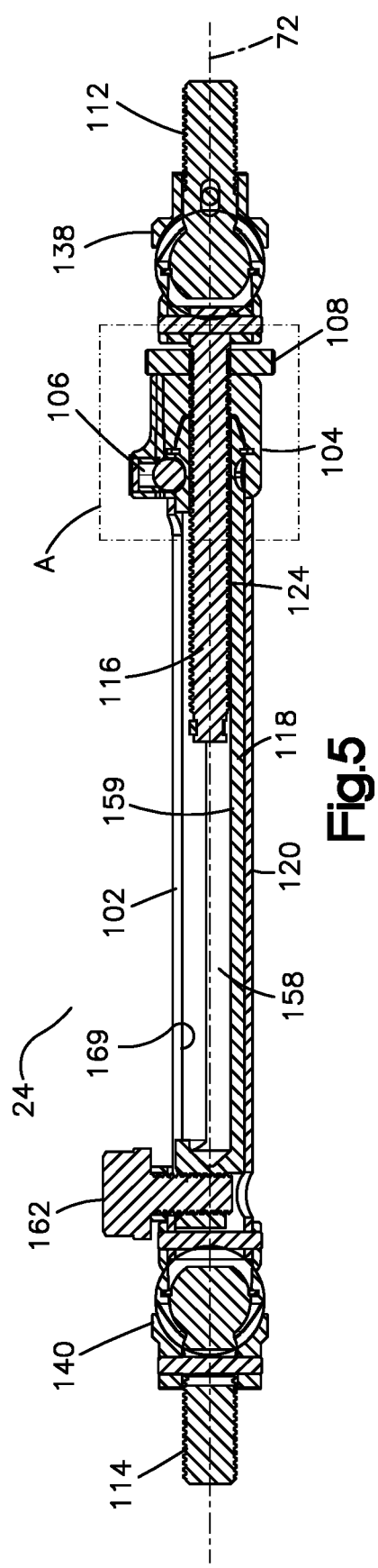

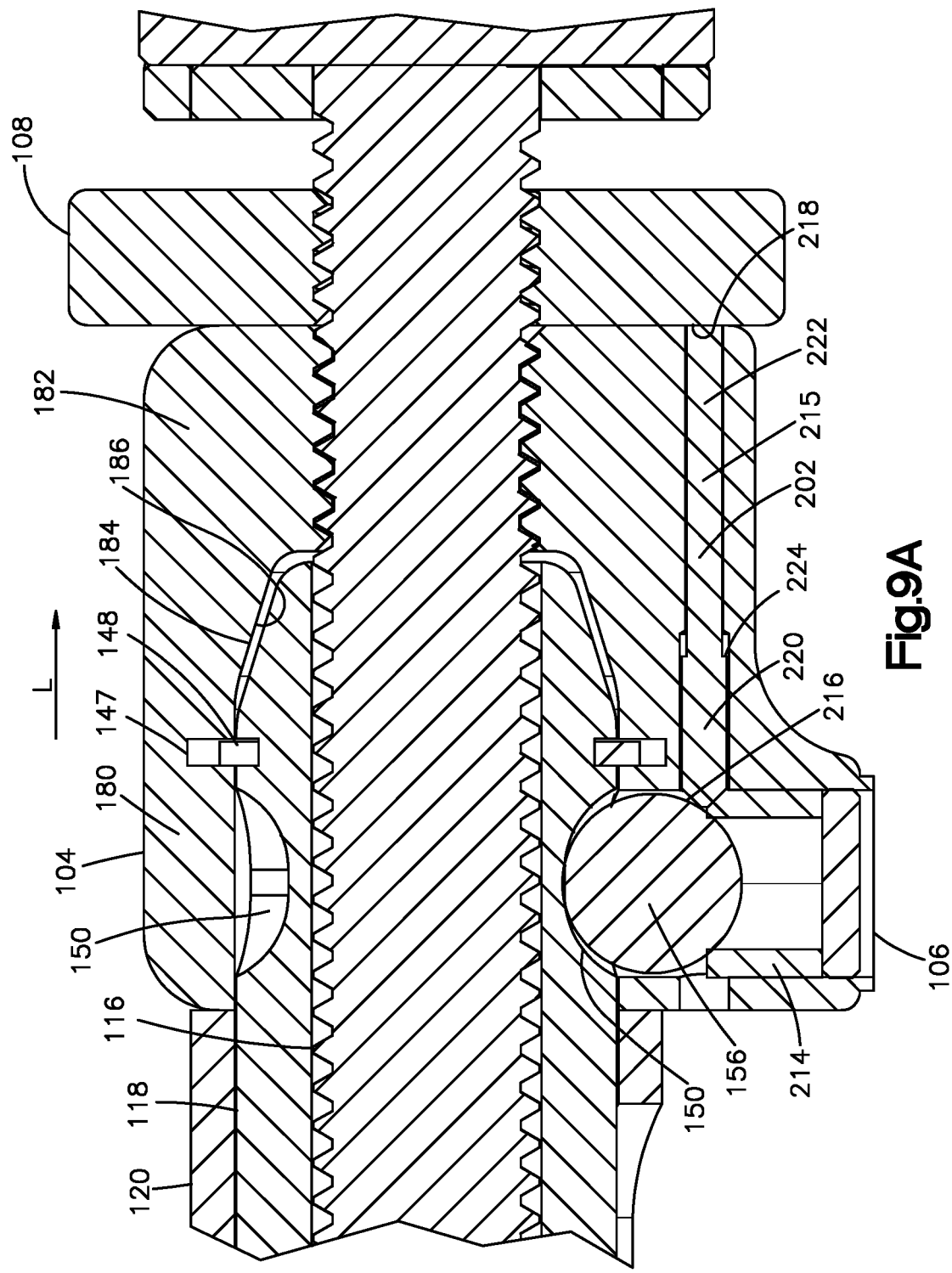

LOCKING SYSTEM AND METHOD

TECHNICAL FIELD

The present invention relates to a locking system and method used to control devices for repairing of fractures or deformities in bones.

BACKGROUND

External bone fixation devices are used to stabilize bone segments and to facilitate the healing of bones at a bone repair site. A bone repair site can include a location of a deformity in a bone or an area of injury to a bone. Distraction and reduction/compression devices may be incorporated into an external bone fixation device and may be used to gradually adjust the relative orientation and spacing of portions fo the bone on opposite sides of a bone repair site.

An external bone fixation device can include a number of support members configured to be connected to the portions of the bone on opposite sides of the bone repair site, as well as a number of distraction and reduction/compression devices configured to adjust the distance between the support members of the external bone fixation device that are attached to the bone portions on opposite sides of the bone repair site. The distraction devices are configured to move the support members gradually over a determined amount of time. The gradual separation allows new bone to form in the void of the bone repair site. In other cases, reduction or compression across a bone repair site to hold the bone portions together is desired to facilitate healing. Such adjustments, whether distraction or reduction/compression, typically follow a prescribed protocol, or treatment plan. After each adjustment, the distraction and reduction/compression device is typically held fixed for a time allowing the new bone to grow and gain strength. After the bone repair site has healed, the external bone fixation device is removed from the bone portions.

During use of the external bone fixation device, varying pressures and forces are applied to the device at the bone repair site. The pressures and forces can cause the distraction and reduction/compression devices to loosen and adversely affect the positioning and spacing of the external fixation device. Additionally, external bone fixation devices are susceptible to inadvertent contact that can also adversely affect the adjustment (e.g. loosen) of the distraction and reduction/compression devices.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

The foregoing needs are met, to a great extent, by the distraction and reduction/compression device and method disclosed in the present application.

According to an embodiment of the present disclosure, a strut assembly is provided that is configured to be connected to a pair of external bone fixation members along a strut axis. The strut assembly comprises a sleeve, a rod, an actuator and a lock member. The sleeve includes a sleeve body and a sleeve bore that extends through the sleeve body along the strut axis. The rod is rotatably fixed with respect to the sleeve. The rod has a threaded outer surface and extends through the sleeve bore along the strut axis such that the rod is translatable relative to the sleeve along the strut axis.

The actuator includes an actuator body and an inner actuator surface that defines an actuator bore that extends through the actuator body along the strut axis. The inner actuator surface is threadedly engaged with the threaded outer surface of the rod, such that rotation of the actuator about the strut axis relative to the rod causes the rod to translate relative to the actuator through the actuator bore and relative to the sleeve through the sleeve bore thereby adjusting a length between the bone fixation members along the strut axis.

The lock member is configured to transition between a locked position in which the lock member engages both the sleeve and the actuator so as to prevent relative rotation between the actuator and the rod, and an unlocked position whereby the lock member does not prevent relative rotation between the actuator and the rod.

According to another embodiment of the present disclosure, a strut assembly is provided and extends along a strut axis. The strut assembly comprises a rod, a sleeve, an actuator, a first lock member, and a second lock member. The rod has an outer surface that is at least partially threaded. The sleeve defines a bore that extends through the sleeve along the strut axis. The bore is configured to receive at least a portion of the rod within. The sleeve is translatable relative to the rod, and the sleeve is substantially rotationally fixed relative to the rod.

The actuator defines a lock channel that extends at least partially through the actuator. The actuator is linearly engaged with the sleeve such that linear movement of the actuator causes linear movement of the sleeve. The actuator is threadedly engaged with the at least partially threaded portion of the rod such that rotation of the actuator relative to the rod about the strut axis causes the actuator and the sleeve to translate along the strut axis relative to the rod.

The first lock member is positioned at least partially within the lock channel of the actuator. The first lock member is configured to transition between a locked position and an unlocked position. In the locked position, the lock member substantially prevents rotation between the sleeve and the actuator. In the unlocked position, the actuator is substantially free to rotate about the sleeve.

The second lock member is threadedly engaged with the at least partially threaded portion of the rod such that rotation of the second lock member relative to the rod about the strut axis causes the second lock member to translate relative to the rod. The second lock member is configured to transition between a retain position and a release position. In the retain position, the second lock member substantially prevents the first lock member from transitioning from the lock position to the unlock position. In the release position the first lock member is substantially free to transition between the locked position and the unlocked position.

According to another embodiment of the present disclosure, an external bone fixation device is provided. The bone fixation device comprising a first external bone fixation member, a second bone fixation member, and a strut assembly. The strut assembly extends along a strut axis, and is configured to be connected between the first and the second external bone fixation members. The strut assembly includes a rod, a sleeve, an actuator, and a lock member.

The rod is elongate along the strut axis and has an outer surface that is at least partially threaded. The sleeve defines a bore that extends through the sleeve along the strut axis. The bore being configured to receive at least a portion of the rod such that the rod is translatable relative to the sleeve along the strut axis. The sleeve is substantially rotationally fixed relative to the rod.

The actuator is linearly engaged with the sleeve such that linear movement of the actuator along the strut axis causes linear movement of the sleeve along the strut axis. The actuator is threadedly engaged with the threaded portion of the rod such that rotation of the actuator relative to the rod about the strut axis causes the actuator and the sleeve to translate along the strut axis relative to the rod.

The lock member is configured to transition between a locked position and an unlocked position. In the locked position, the lock member engages both the sleeve and the actuator such that rotation between the sleeve and the actuator is substantially prevented. In the unlocked position, the lock member is spaced apart from the sleeve such that the actuator is substantially free to rotate about the sleeve.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 4 illustrates a side elevation view of the strut shown in FIG. 3A;

FIG. 5 illustrates a cross-sectional view of the strut shown in FIG. 4 taken along line 5-5;

FIG. 9A illustrates a close-up view of a cross-section of the strut shown in FIG. 5 defined by the box A in a first configuration (e.g. locked configuration)

DETAILED DESCRIPTION OF ILLUSTRATIVE EMBODIMENTS

Figure 1A:
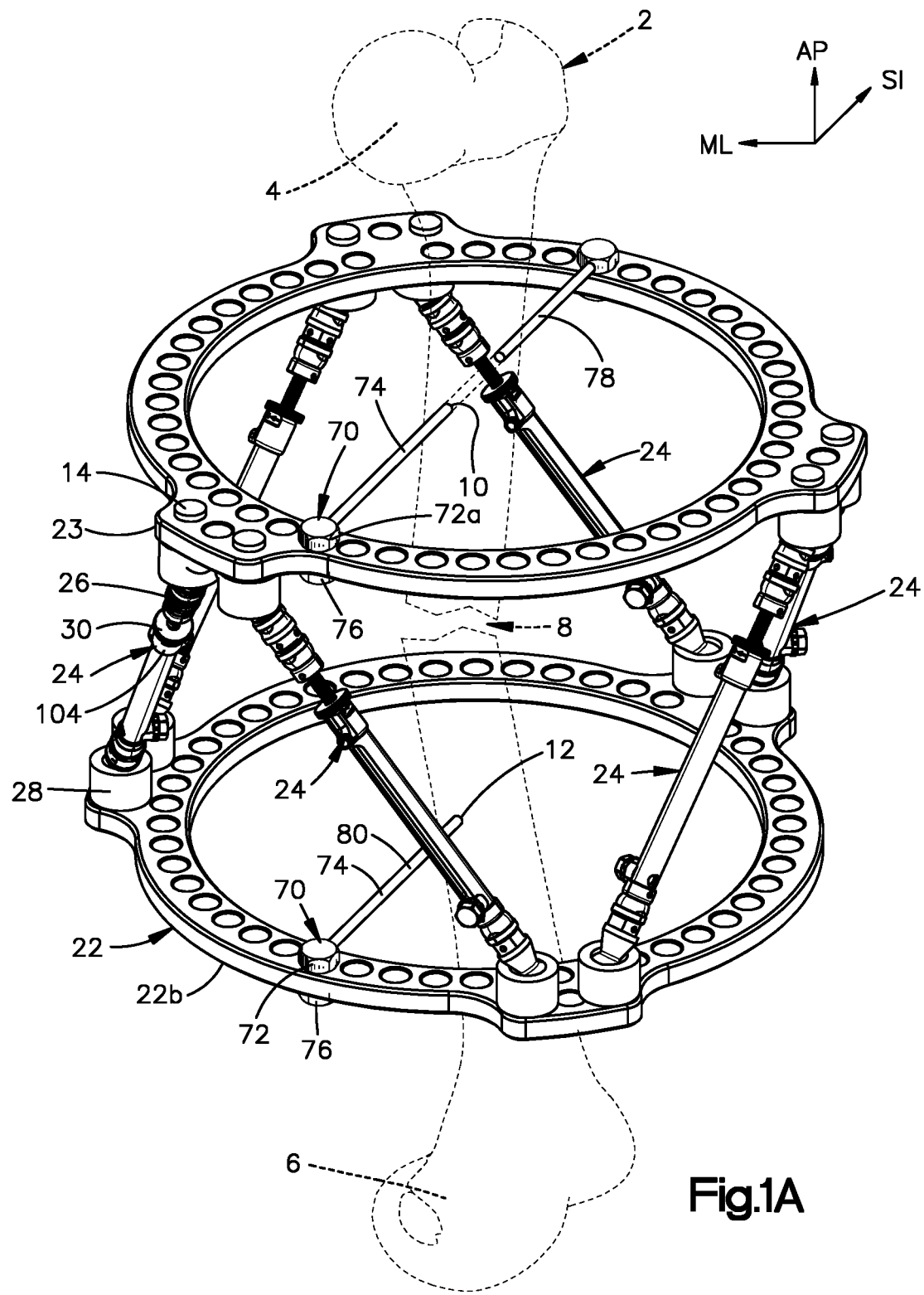
FIG. 1A is a perspective view of an external bone fixation device in a first configuration, positioned proximate a fractured bone, according to an aspect of this disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

Certain terminology used in this description is for convenience only and is not limiting. The words "top", "bottom", "distal", "proximal", "leading", "trailing", "inner", "outer", "above", "below", "axial", "transverse", "circumferential," and "radial" designate directions in the drawings to which reference is made. The words "inner", "internal", and "interior" refer to directions towards the geometric center of the implant and/or implant adjustment tools, while the words "outer", "external", and "exterior" refer to directions away from the geometric center of the implant and/or implant adjustment tools. The words, "anterior", "posterior", "superior," "inferior," "medial," "lateral," and related words and/or phrases are used to designate various positions and orientations in the human body to which reference is made. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. The term "substantially" is intended to mean considerable in extent or largely but not necessarily wholly that which is specified. All ranges are inclusive and combinable. The terminology includes the above-listed words, derivatives thereof and words of similar import.

Figure 1B:
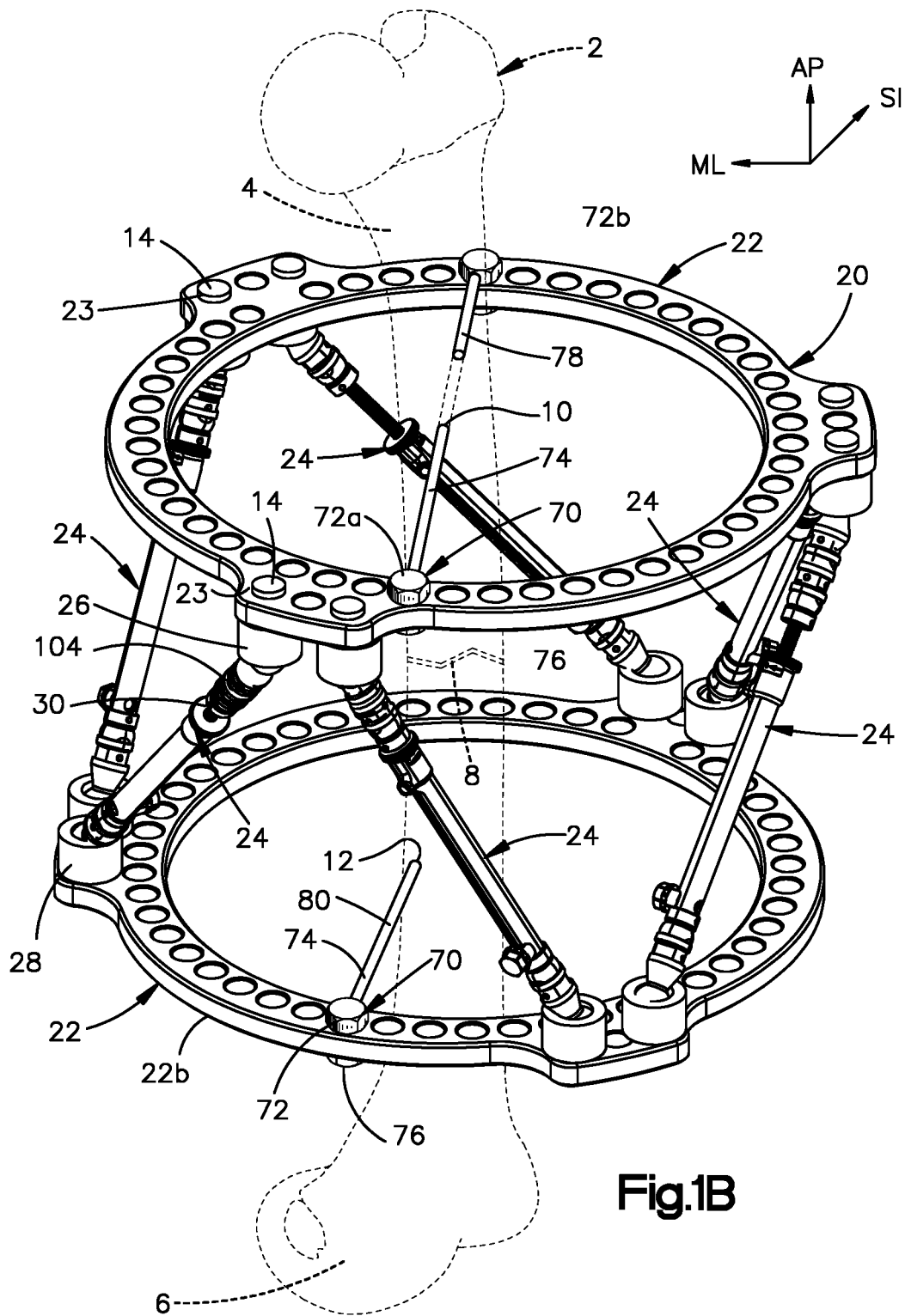
FIG. 1B is a perspective view of the external bone fixation device shown in FIG. 1A in a second configuration positioned proximate the fractured bone.

FIG. 1A illustrates a perspective view of an external bone fixation device 20 (also referred to as "device 20") in a first configuration, positioned proximate a fractured bone 2. FIG. 1B illustrates a perspective view of the external bone fixation device 20 illustrated in FIG. 1A in a second configuration positioned proximate the fractured bone 2. The device 20 is configured to be used to correct bone deformities, which can be anatomical deformities or bone injuries such as fractures. In one embodiment the external bone fixation device 20 can be used to treat a bone 2, for example a fractured long bone such as a femur. The bone 2 can include a first bone portion 4, such as a proximal portion, and a second bone portion 6, such as a distal portion. The first bone portion 4 and the second bone portion 6 can be separated by a defect, such as a fracture 8. The device 20 is configured to attach to the bone 2 at a first location 10 located on the first bone portion 4, and at a second location 12 located on the second bone portion 6. The device 20 is configured to move at least one or both of the first bone portion 4 and the second bone portion 6 relative to the other of the first bone portion 4 or the second bone portion 6, respectively, from a first position, such as a first orientation as shown in FIG. 1A, to a second position that is different from the first position, such as a second orientation different from the first orientation as shown in FIG. 1B, to align the first and second bone portions 4 and 6 so as to assist in correction the bone deformity of the bone 2.

As shown in the illustrated embodiment, the device 20 can include a plurality (e.g., a pair or more) of external bone fixation members, such as bases 22, that are each configured to be secured to respective bone portions, and at least one strut 24, such as a plurality of struts 24, that are configured to attach to at least a pair of the external bone fixation members at attachment locations 23. One or more fasteners 14, for example bolts or screws, can be used to secure the strut 24 relative to the base 22 at the attachment location 23. The external support members can attach to a bone fixation element 74 that is anchored in the respective bone portion. For instance, the external support member can be supported outboard of the epidermis that surrounds the bone portion, and the bone fixation element 74 can extend from the external support member, through the epidermis and soft tissue disposed between the epidermis and bone portion, and into the bone portion.

For example, the bases 22 can include a first base 22a and a second base 22b. The struts 24 can define respective distraction and reduction/compression devices (collectively referred to herein as "strut" or "struts" 24) configured to attach adjacent ones of the plurality of bases 22 such that the adjacent bases 22 are movable relative to one another. For instance, the struts 24 define a length between the attachment locations 23 that can be adjustable so as to cause at least one of the bases 22 to move relative to the other of the bases 22 at the respective attachment locations 23.

In particular, an increase of the length of the struts 24 can cause one of the attachment locations 23 to move away from the other of the attachment locations, a decrease of the length of the struts 24 can cause one of the attachment locations 23 to move toward the other of the attachment locations 23, and any adjustment of the length (increase or decrease) can cause at least one of the external fixation members to rotate relative to the other of the external fixation members. Each of the struts 24 includes a first end portion 26 configured to be attached to a first of the adjacent bases 22, for example the first base 22a at the attachment location 23, and a second end portion 28 configured to be attached to a second of the adjacent bases 22, for example the second base 22b at the attachment location 23. The struts 24 can further include a strut axis 72 (as shown in FIG. 5), the strut axis 72 extends from the first end portion 26 to the second end portion 28 such that the strut 24 is elongate along the strut axis 72.

The strut 24 includes an intermediate portion 30 disposed between the first end portion 26 and the second end portion 28. The strut 24 can further include an actuator 104, such that when the actuator 104 is actuated, the first end portion 26 moves relative to the second end portion 28. In one embodiment, the intermediate portion 30 carries or supports the actuator 104, as shown. Actuation, for example rotation, of the actuator 104 of the strut 24 moves the first end portion 26 relative to the second end portion 28. When the first end portion 26 is attached to the first base 22a and the second end portion 28 is attached to the second base 22b, actuation of the actuator 104 moves the first end portion 26 and the attached first base 22a relative to the second end portion 28 and the attached second base 22b.

The device 20 is configured such that in an assembled configuration, wherein the first end portions 26 and the second end portions 28 of the struts 24 are attached to the first base 22a and the second base 22b, the first base 22a is moveable relative to the second base 22b in up to six degrees of freedom. For example, the first base 22a can translate relative to the second base 22b in either the anterior-posterior direction AP, the medial-lateral direction ML, the superior-inferior direction SI, or any combination thereof. In addition, the first base 22a can rotate relative to the second base 22b about an axis defining the anterior-posterior direction AP, the medial-lateral direction ML, the superior-inferior direction SI, or any combination thereof.

The rotational locking of the strut 24 when attached to one of the bases 22 at both the first and second end portions 26 and 28 may be desired in an application where a certain orientation of the struts 24 relative to the bases 22 is desired. For example, the struts 24 can include visual indications regarding the properties of the strut 24, such as the current length of the strut. The rotational locking of the strut 24 as described above allows a user to have the visual indications facing in a direction that are easily readable by a user when the external bone fixation device 20 is attached to the bone 2.

The device 20, in one embodiment, includes a plurality of attachment mechanisms 70 that are configured to attach the first bone portion 4 to the first base 22a and the second bone portion 6 to the second base 22b such that as the first and second bases 22a and 22b move relative to one another, the first and second bone portions 4 and 6 also move relative to one another. In other words the attachment mechanisms 70 are configured to attach a base 22 to a portion of the bone 2 such that the base 22 and the portion of the bone 2 are translationally and rotationally coupled together.

As shown in the illustrated embodiment, the attachment mechanisms 70 can include a bracket 72 that can be attached to the base 22, for example by a fastener 76. The attachment mechanism 70 further includes the bone fixation element 74 that couples the bracket 72 to the bone 2. The bone fixation element 74 includes, for example, a wire 78 and a rod 80. In one embodiment, the wire 78 is a Kirschner wires (or "K-wire"). As shown, the wire 78 is configured to be attached to a first bracket 72a, extend completely through the bone 2, and be attached to a second bracket 72b on the other side of the bone 2. The rod 80 is configured to be attached to a bracket 72, and extend into, or partially through, the bone 2. As shown, the rod 80 is only attached to one bracket 72. The rod 80 can be threaded or have another retention structure on an end of the rod 80 that is inserted into the bone 2 that aids in securing the rod 80 to the bone 2.

Figure 2:
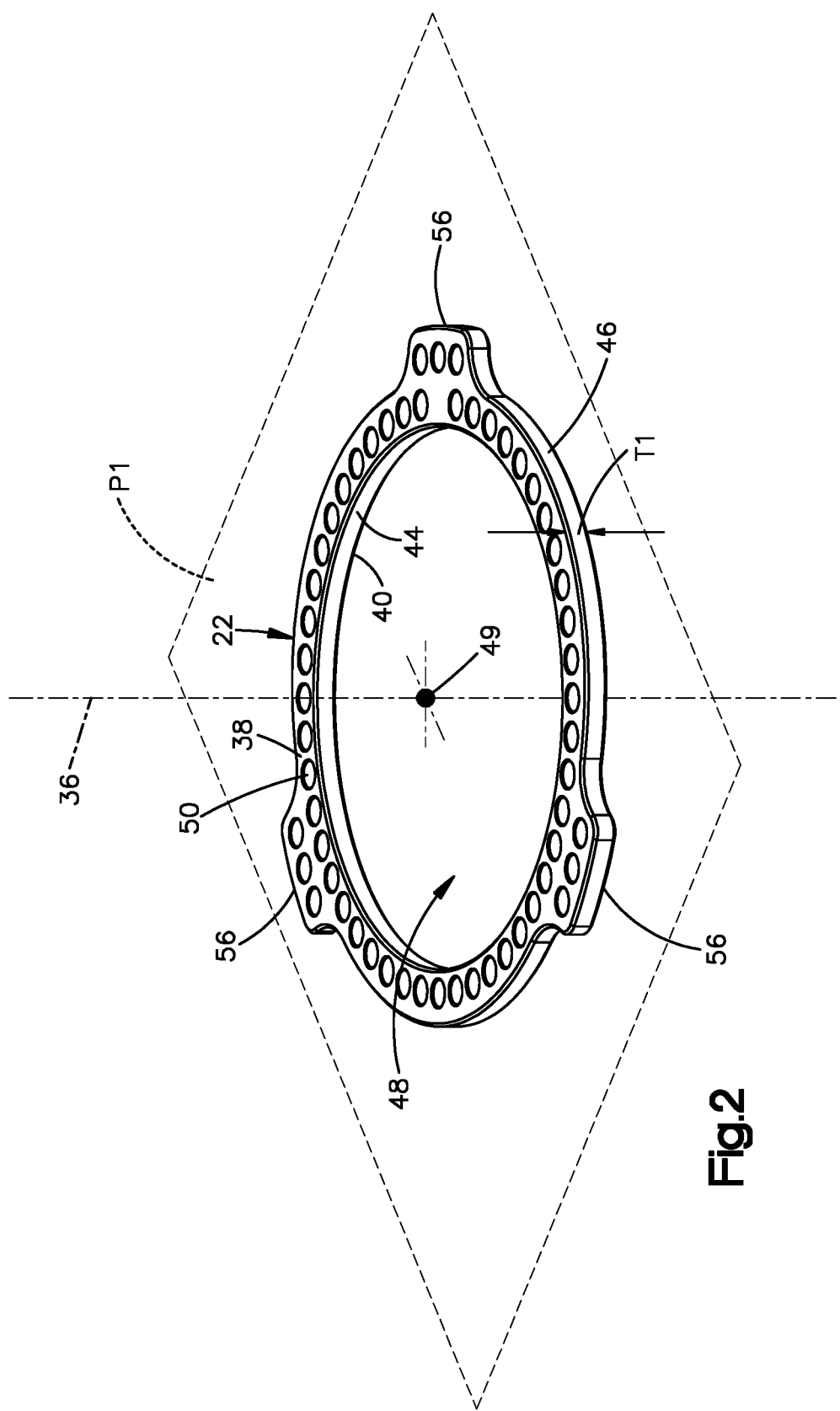
FIG. 2 illustrates a perspective view of a base of the external bone fixation device shown in FIG. 1A, according to an aspect of this disclosure.

FIG. 2 illustrates a perspective view of the base 22, according to an aspect of this disclosure. The base 22 includes a base body 34. As shown in the illustrated embodiment, the base body 34 can be substantially ring shaped. The base body 34 can be formed from a monolithic piece of material, as shown, or the base body 34 can be formed from separate pieces or segments of material that are joined together. The base 22 can include a base axis 36. In one embodiment, the base axis 36 is a central axis such that the base body 34 is substantially centered about the base axis 36. The base body 34 includes a first surface 38 (or upper surface), a second surface 40 (or lower surface) that is opposite the first surface 38, and a thickness T1 measured from the first surface 38 to the second surface 40. In one embodiment the thickness T1 is constant throughout the base body 34. In another embodiment the thickness T1 is not constant throughout the base body 34.

As shown in the illustrated embodiment, the first surface 38 is substantially planar such that the first surface 38 defines a plane P1. In another embodiment, the second surface 40 is substantially planar such that the second surface 40 defines the plane P1. In another embodiment both the first surface 38 and the second surface 40 are substantially planar such that either the first surface 38 or the second surface 40, or both define the plane P1.

The device 20 includes more than one base 22. As shown, the device includes the first base 22a and the second device 22b. The first base 22a and the second base 22b are configured to be attached to the first bone portion 4 and second bone portion 6 of a bone 2, respectively. When the first base 22a and the second base 22b are first attached to the first and second bone portions 4 and 6, the first and second bone portions 4 and 6 are in a first orientation relative to one another. When the first and second bases 22a and 22b are attached to the first and second bone portions 4 and 6 in the first orientation, the first and second bone portions 4 and 6 are in an undesired position such that the planes P1 of the first and second bases 22a and 22b are non-parallel to one another, the base axes 36 of the first and second bases 22a and 22b are non-parallel, or both.

After the first and second bases 22a and 22b are secured to the first and second bone portions 4 and 6 in the first configuration, a treatment plan can be performed to move the first and second bases 22a and 22b into a second orientation. In the second orientation, the first and second bone portions 4 and 6 are in a desired position such that the planes P1 of the first and second bases 22a and 22b are substantially parallel to one another, the base axes 36 of the first and second bases 22a and 22b are substantially parallel, or both. As will be described in detail below, the treatment plan can include actuation of the actuators 104 of the struts 24. In one embodiment the treatment plan includes actuation of the actuators 104 of specified struts 24, a specified amount, over a specified amount of time.

Referring to FIG. 2, the base body 34 further includes a first side wall 44, such as an outer side wall, and a second side wall 46, such as an inner side wall, that is opposite the first side wall 44. As shown in the illustrated embodiment, the first side wall 44 defines an outer periphery of the base body 34, and the second side wall 46 defines an inner periphery of the base body 34. The base 22 can further include an opening 48. The opening 48 is defined by the base body 34, for example the second side wall 46, and the opening 48 is configured to receive the bone 2. The base body 34 defines a width measured from the second side wall 46 to the first side wall 44 in a direction perpendicular to the base axis 36. In one embodiment the width is constant throughout the base body 34. In another embodiment the width W1 is not constant throughout the base body 34.

In one embodiment, the base body 34 includes at least one tab 56. The tab 56 includes a portion of the base body 34 that extends radially outward from the base axis 36 farther than a surrounding portion of the base body 34. As shown, the tab 56 defines a portion of the base body 34 with a greater width than the width of the base body 34 at a location adjacent the tab 56. The base body 34 can include any number of tabs 56 (including no tabs), spaced about the base body 34 in any desired configuration. For example, the base body 34 can include three tabs 56 spaced apart substantially equally about the outer periphery of the base body 34, such that each of the tabs 56 is spaced about 120 degrees from each of the other two tabs 56.

The base 22 also includes a plurality of holes 50. The plurality of holes 50 extend through the base body 34, for example the holes 50 extend though an entirety of the thickness of the base body 34 from the first surface 38 to the second surface 40. The holes 50 are configured to receive the struts 24 and the attachment mechanisms 70. The holes 50 can be threaded, unthreaded, or a combination of threaded and unthreaded such that the holes 50 are configured to receive both locking and non-locking fasteners. In the illustrated embodiment, the holes 50 include a first series of holes spaced radially inward from a second series of holes. It will be appreciated that the holes 50 could include other arrangements that include, for example, additional series of holes, fewer or more holes, different radial and/or circumferential alignments, or still other arrangements.

It will be appreciated that the base 22 can include multiple segments (not shown). For example, the base body 34 can include primary and secondary base bodies that can be joined to form a complete ring. Multiple segments can provide additional flexibility or options when the device 20 is being assembled and attached to a patient. For example, the primary base body can be placed in a desired position relative to a bone and the secondary base body can be attached to the primary base body in the desired position without having to traverse the base 22 all the way from a distal end of the bone (or appendage) to the desired position. The base 22 can include other configurations, shapes, and or orientations to facilitate attachment to a patient. For example, the base 22 can include an approximate u-shape to be place around an appendage, such as a foot such that the base 22 is positioned posterior to (or behind) a heel of a foot, and a gap of the base 22 is positioned to receive an anterior portion, such as the toes of the foot.

Figure 3A:
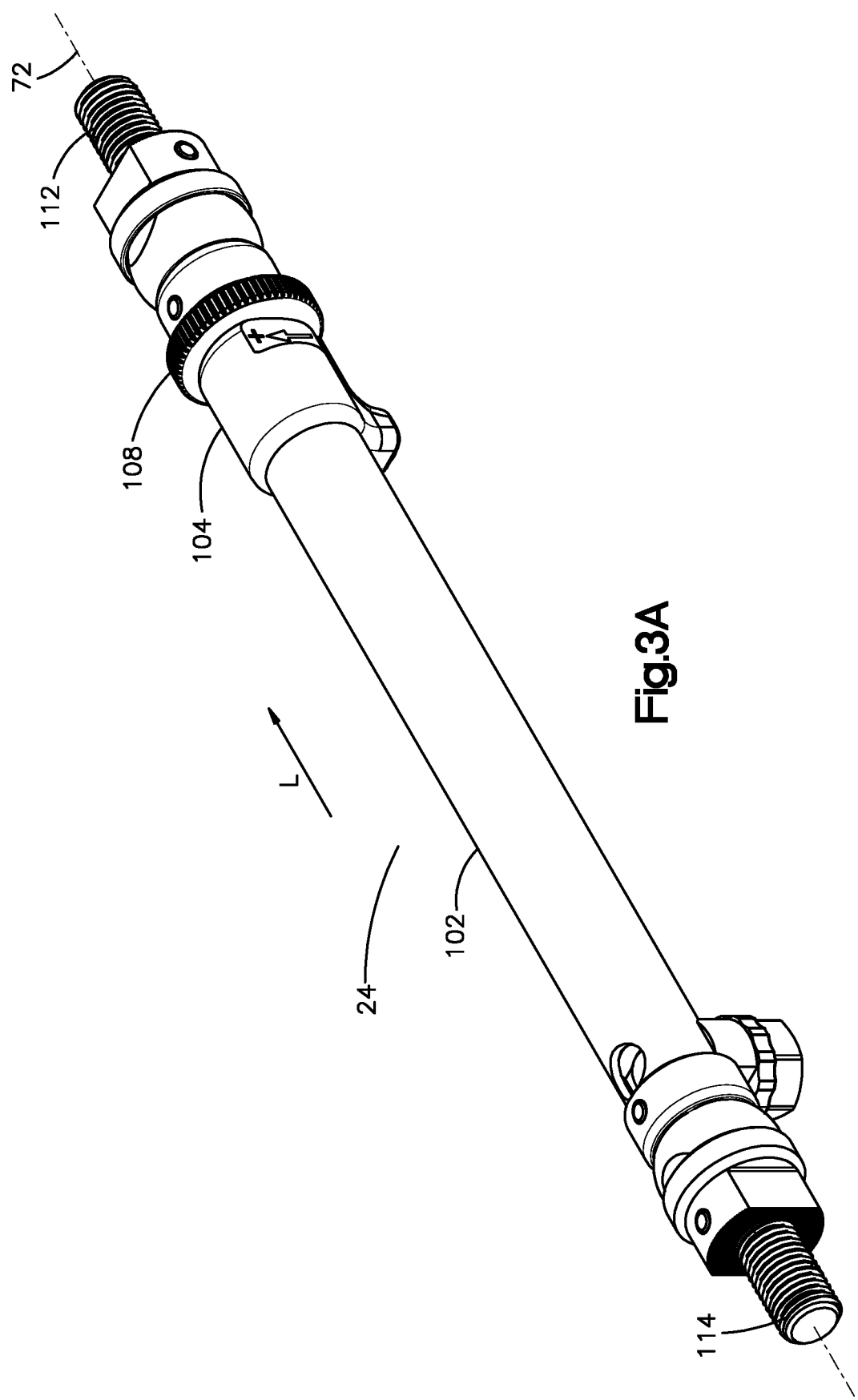
FIG. 3A illustrates a top perspective view of a strut, according to an aspect of this disclosure.
Figure 3B:
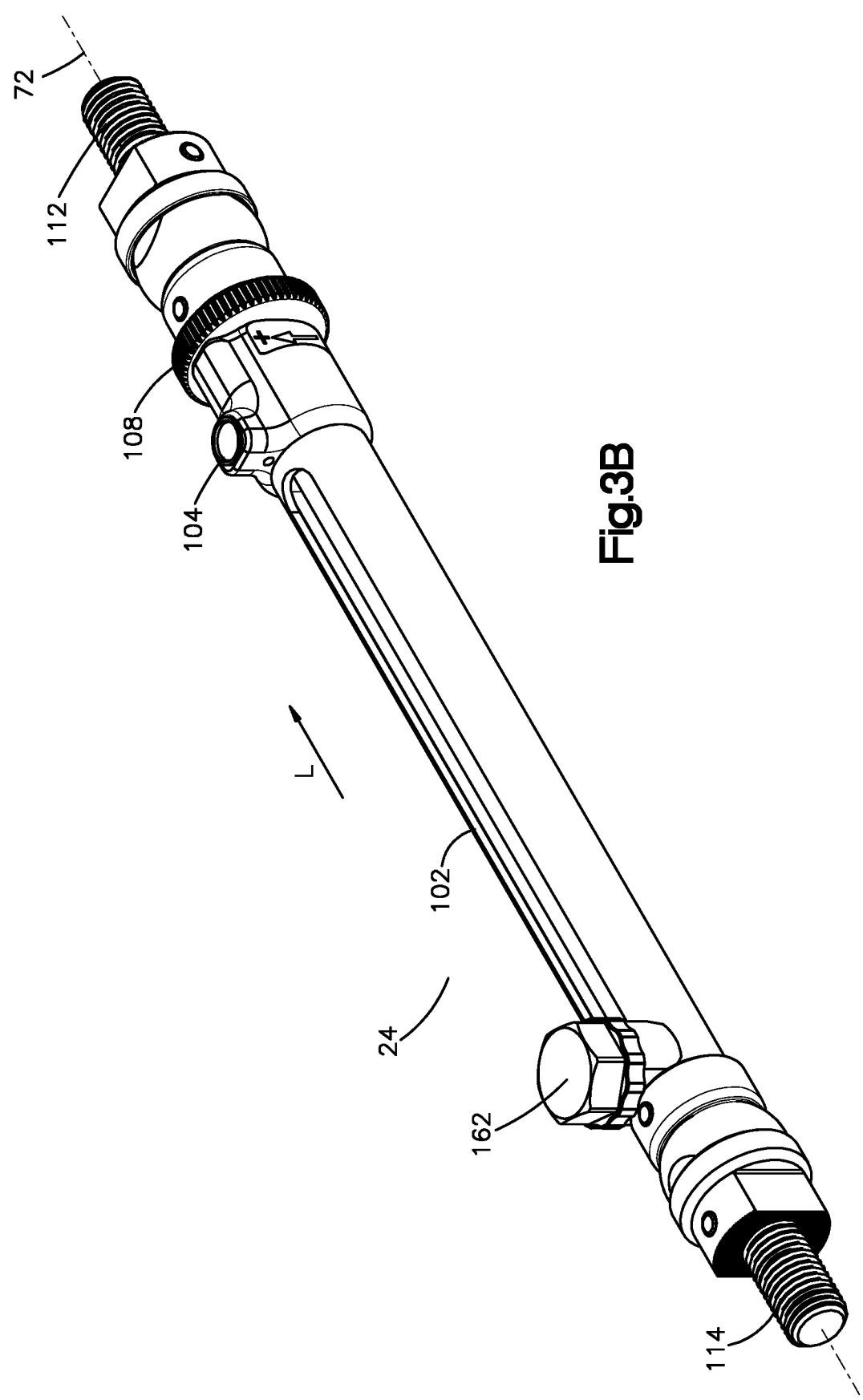
FIG. 3B illustrates a bottom perspective view of the strut shown in FIG. 3A.
Figure 6:
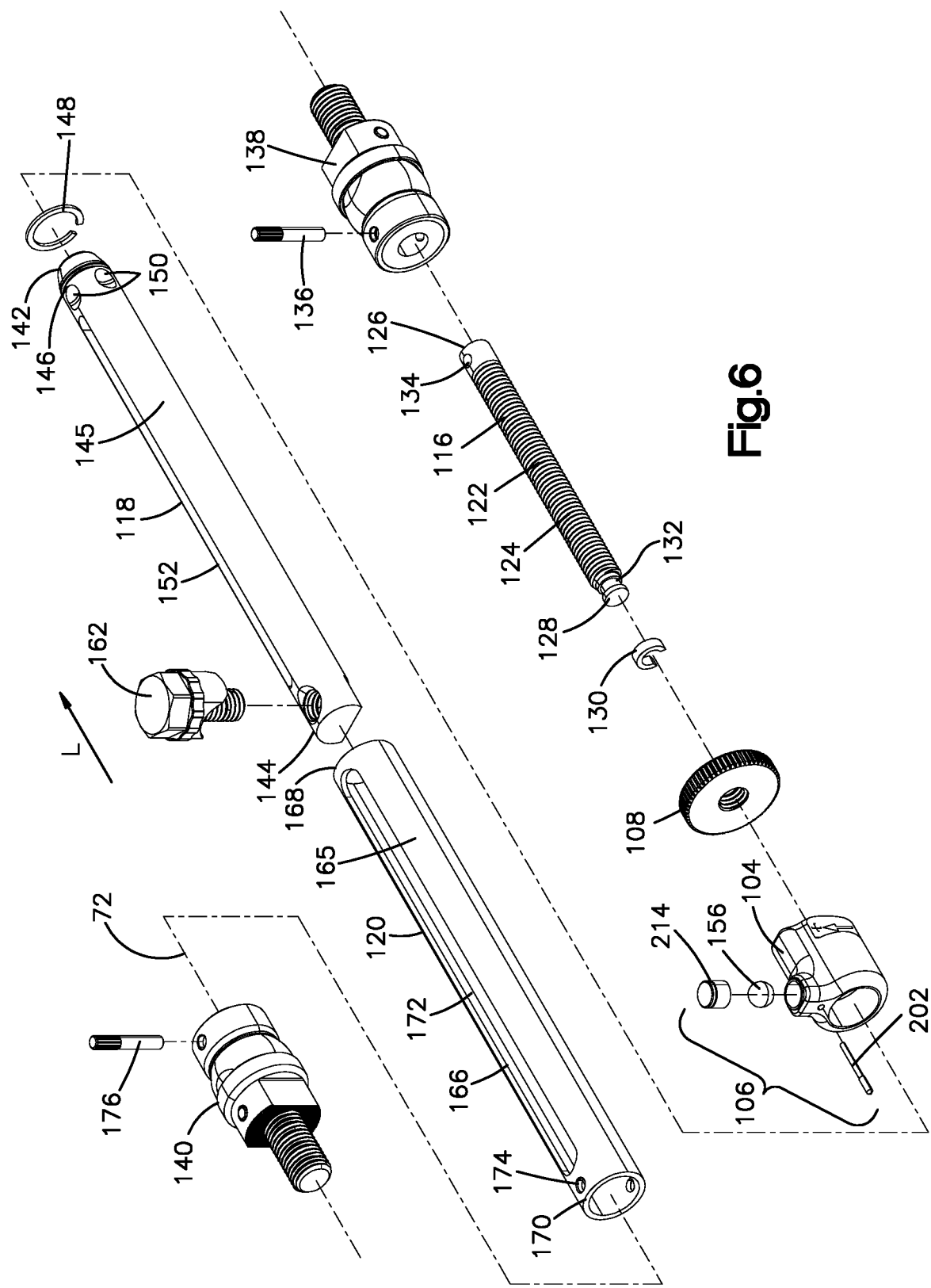
FIG. 6 illustrates an exploded bottom perspective view of the strut shown in FIG. 3A.

FIG. 3A illustrates a top perspective view of the strut 24, FIG. 3B illustrates a bottom perspective view of the strut 24, FIG. 4 illustrates a side elevation view of the strut 24, FIG. 5 illustrates a cross-sectional view of the strut 24 taken along line 5-5 shown in FIG. 4, and FIG. 6 illustrates an exploded bottom perspective view of the strut 24. The strut 24 includes a strut body 102, the actuator 104, a locking assembly 106, and a nut lock member 108. The strut 24 includes a first end 112 and a second end 114 spaced from the first end along a strut axis 72. The strut 24 can be elongate along the strut axis 72 as shown in the illustrated aspects. The strut axis 72 can be a central axis, and the strut axis 72 can be parallel to a longitudinal direction L. The strut 24 defines a length $D_1$ measured from the first end 112 to the second end 114. The length $D_1$ being measured along the strut axis 72. Actuation of the actuator 104 causes the strut 24 to change the length $D_1$, as further described below.

The strut body 102 can include a rod 116, a sleeve 118, and a housing member 120. The rod 116 and the sleeve 118 are configured to be connected such that the rod 116 and the sleeve 118 are translatable relative to one another along the strut axis 72. The actuator 104 is coupled to the strut 24 such that actuation of the actuator 104 translates the rod 116 relative to the sleeve 118.

The rod 116 can be elongate along the strut axis 72, and include an outer surface 122 that defines a threaded portion 124. The outer surface 122 of the rod 116 can be either wholly or partially threaded. The rod 116 includes a first end 126 and a second end 128 spaced from the first end 126 along the strut axis 72. The second end 128 is configured to receive an alignment member 130. For example, the second end 128 can define a recess 132 configured to receive the alignment member 130 within. The alignment member is configured to align the rod 116 within the sleeve 118. The first end 126 can define a receiving hole 134 extending therethrough. The receiving hole 134 is configured to receive a retention member 136 (e.g. a pin) within to connect the rod 116 to a first rotation assembly 138. The retention member 136 can linearly and rotationally fix the rod 116 to the first rotation assembly 138.

The sleeve 118 includes a first end 142 and a second end 144 spaced from the first end 142 along the strut axis 72. The sleeve 118 can include a circumferential groove 146 positioned toward the first end 142 of the sleeve. The groove 146 is defined by an outer surface 145 of the sleeve 118 and is configured to receive a retention member 148 within. The retention member 148 positioned within the groove 146 is configured to secure the sleeve 118 to the actuator 104. The sleeve 118 is configured to connect to the actuator 104 such that the actuator 104 is translationally fixed relative to the sleeve 118, and rotatable about the strut axis 72 relative to the sleeve 118. As shown in the illustrated aspect, retention member 148 comprises a c-clip that is at least partially received within the groove 146 of the sleeve 118 and at least partially received within a circumferential groove 147 of the actuator 104.

The outer surface 145 of the sleeve 118 further defines at least one detent 150. The at least one detent 150 can comprise a plurality of detents 150. The plurality of detents 150 can be spaced circumferentially about the strut axis 72. In an aspect, each of the plurality of detents 150 is spaced equidistant from each of the other detents 150. Each of the plurality of detents 150 can be shaped and sized substantially similarly as each of the other plurality of detents 150. For example, all of the plurality of detents can have either a hemispherical shape, rectangular shape, trapezoidal shape, or other shape. The configuration of the plurality of detents 150 corresponds to a configuration of a lock member 156 (e.g. first lock member) of the lock assembly 106 such that the lock member 156 is receivable within the plurality of detents 150. The lock member 156 is configured to selectively rotationally lock the sleeve 118 to the actuator 104, as further described below.

The sleeve 118 includes an inner surface 159 opposite the outer surface 145. The inner surface 159 defines a bore 158 that extends longitudinally into and at least partially through the sleeve 118 from the first end 142 toward the second end 144. The sleeve 118 defines a tube-like body structure configured to receive the rod 116 at least partially within.

The sleeve 118 further includes a receiving hole 160 that extends at least partially through the sleeve along an axis that is substantially perpendicular to the strut axis 72. The receiving hole 160 is located toward the second send 144 of the sleeve 118. The receiving hole 160 is configured to receive a follower 162 within, to substantially secure the follower 162 to the sleeve 118. The receiving hole 160 can include internal threads that correspond to external threads on the follower 162. The follower 162 is configured to prevent the sleeve 118 from rotating relative to the housing member 120 as the sleeve 118 translates relative to the housing member 120. For example, the follower 162 can be positioned through a housing slot 166 and into the receiving hole 160 of the sleeve 118. When the follower 162 is loosened within the receiving hole 160, the sleeve 118 can linearly translate along the strut axis 72 relative to the housing member 120 such that the follower 162 translates within the housing slot 166, while the housing slot 166 prevents the sleeve 118 from rotating. When the follower 162 is tightened within the receiving hole 160, the sleeve 118 is translationally and rotationally fixed to the housing member 120.

In an alternative aspect, the rod 116 can define a receiving hole configured to receive the follower 162 within. The follower 162 can be positioned through a sleeve slot 152 defined by the sleeve 118 and into the receiving hole of the rod 116. When the follower 162 is loosened within the receiving hole of the rod 116, the sleeve 118 can linearly translate along the strut axis 72 relative to the rod 116 such that the follower 162 translates within the sleeve slot 152, while the sleeve slot 152 prevents the sleeve 118 from rotating relative to the rod 116 (e.g. the sleeve 118 is rotationally fixed to the rod 116 via the follower 162). When the follower 162 is tightened within the receiving hole of the rod 116, the sleeve 118 is translationally and rotationally fixed to the rod 116.

The outer surface 145 of the sleeve 118 defines the sleeve groove 152. The sleeve groove 152 extends between the first and second ends 142 and 144 in the longitudinal direction L, and extends through the outer surface 145 into the bore 158 of the sleeve 118.

The housing member 120 includes a first end 168 and a second end 170 spaced from the first end 168 along the strut axis 72. The housing member 120 has an inner surface 169 and an outer surface 165 opposing the inner surface 169. The inner surface 169 defines a bore 172 that extends longitudinally into and at least partially through the housing member 120 from the first end 168 toward the second end 170. The housing member 120 defines a tube-like body structure configured to receive the sleeve 120 at least partially within the bore 172.

The housing member 120 further includes a receiving hole 174 that extends through the housing member 120 from first location on the outer surface 165 to a second location on the outer surface 165. The receiving hole 174 can be located toward the second end 170 of the housing member 120. The receiving hole 174 is configured to receive a retention member 176 (e.g. a pin) within to connect the housing member 120 to a second rotation assembly 140. The retention member 176 can linearly and rotationally fix the housing member 120 to the second rotation assembly 140.

Figure 7:
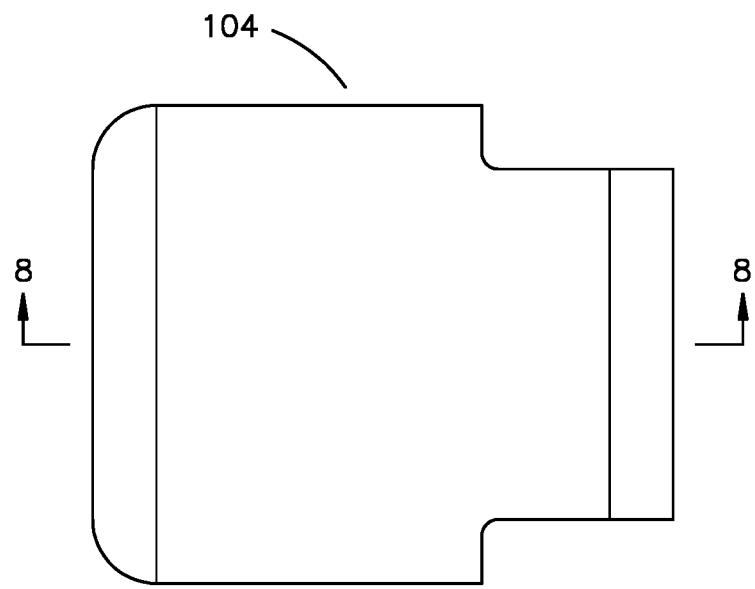
FIG. 7 illustrates a top elevation view of an actuator, according to an aspect of this disclosure.
Figure 8:
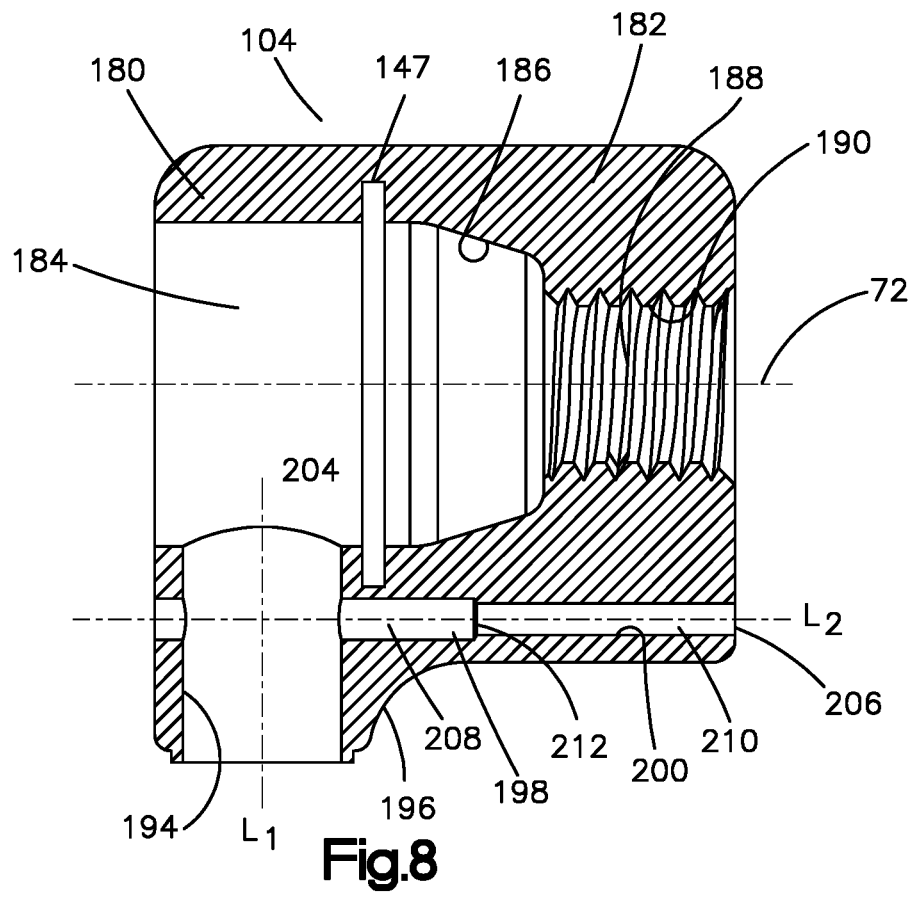
FIG. 8 illustrates a cross-sectional view of the actuator shown in FIG. 7 taken along line 8-8.

FIG. 7 illustrates a top elevation view of the actuator 104, and FIG. 8 illustrates a cross-sectional view of the actuator 104 taken along line 8-8 shown in FIG. 7. The actuator 104 includes a first portion 180 that is configured to receive the first end 146 of the sleeve 118, and a second portion 182 that is configured to receive the threaded rod 116. The first portion 180 can include a recess 184 that is defined by an inner surface 186 of the first portion 180. The inner surface 186 defines the circumferential groove 147 configured to receive the retention member 148 within to linearly fix the actuator 104 to the sleeve 118. The recess 184 can be unthreaded. A shape and/or configuration of the recess 184 can correspond to a shape and/or configuration of the first end 146 of the sleeve 118. For example, if the first end 146 of the sleeve 118 includes a partially conical shape, the recess 184 can include a partially conical shape to receive the sleeve 118 within.

The second portion 182 of the actuator 104 can include a through bore 188 that is defined by an inner surface 190 of the second portion 182. The inner surface 190 of the second portion 182 includes threads that are configured to engage the threaded portion 124 of the rod 116. The inner surface 190 of the second portion 182 defines a circumference, and an entirety of the circumference of at least a portion of the inner surface 190 is threaded. Alternatively, the entirety of the circumference contacts the threaded portion 124 of the rod 116 both when the actuator 104 is rotated in a first direction of rotation about the strut axis 72 and when the actuator 104 is rotated in a second direction of rotation about the strut axis 72 that is opposite the first direction of rotation.

The actuator 104 further includes a first lock channel 192 and a second lock channel 198. The first lock channel 192 is defined by a first lock surface 194. In an aspect, the first lock channel 192 is located in the first portion 180 of the actuator 104. The first lock channel 192 extends from an outer surface 196 of the actuator 104 to the recess 184. When the sleeve 118 is secured within the recess 184 of the actuator 104, the first lock channel 192 aligns the plurality of detents 150 along the strut axis 72. The first lock channel 192 extends along a first lock axis $L_1$. The first lock channel 192 can be substantially cylindrical such that the first lock channel 192 extends circumferentially about the first lock axis $L_1$. The first lock axis $L_1$ is substantially perpendicular to the strut axis 72. In an alternative aspect, the first lock axis $L_1$ may be angled relative to the strut axis 72 at an angle other than 90 degrees. The first lock channel 192 is configured and sized to receive the lock member 156 within, such that the lock member 156 can translate along the first lock axis $L_1$.

The second lock channel 198 is defined by a second lock surface 200. In an aspect, the second lock channel 198 extends through the first and second portions 180 and 182 of the actuator 104 from a first location on the outer surface 196 to a second location on the outer surface 196. It will be appreciated that the second lack channel 198 may extend partially through the actuator 104 from the second portion 182 toward the first portion 180. The second lock channel 198 extends along a second lock axis $L_2$, and intersects with the first lock channel 192. The second lock axis $L_2$ is substantially parallel to the strut axis 72. In an alternative aspect, the second lock axis $L_2$ can be at an angle relative to the strut axis 72 such that the second lock axis is not substantially parallel to the strut axis 72. The second lock axis $L_2$ is angularly offset from the first lock axis $L_1$. In an aspect, the second lock axis $L_2$ is substantially perpendicular to the first lock axis $L_1$.

The second lock channel 198 is configured and shaped to receive an interference member 202 of the locking assembly 106 within. The second lock channel 198 extends from a first channel opening 204 defined by the first lock surface 194 of the actuator 104 to a second channel opening 206 defined by the outer surface 196 of the actuator 104. The second lock channel 198 includes a first channel portion 208 and a second channel portion 210. The first channel portion 208 extends from the first channel opening 204 to the second channel portion 210. The second channel portion 210 extends from the first channel portion 208 to the second channel opening 206. The first channel portion 208 has a cross-sectional dimension that is greater than a cross-sectional dimension of the second channel portion 210. A channel shoulder 212 is defined between the first and second channel portions 208 and 210. The channel shoulder 212 can extend about the second lock axis $L_2$. The channel shoulder 212 is configured to affect movement of the interference member 202 positioned within the second lock channel 198, as further described below.

Figure 9B:
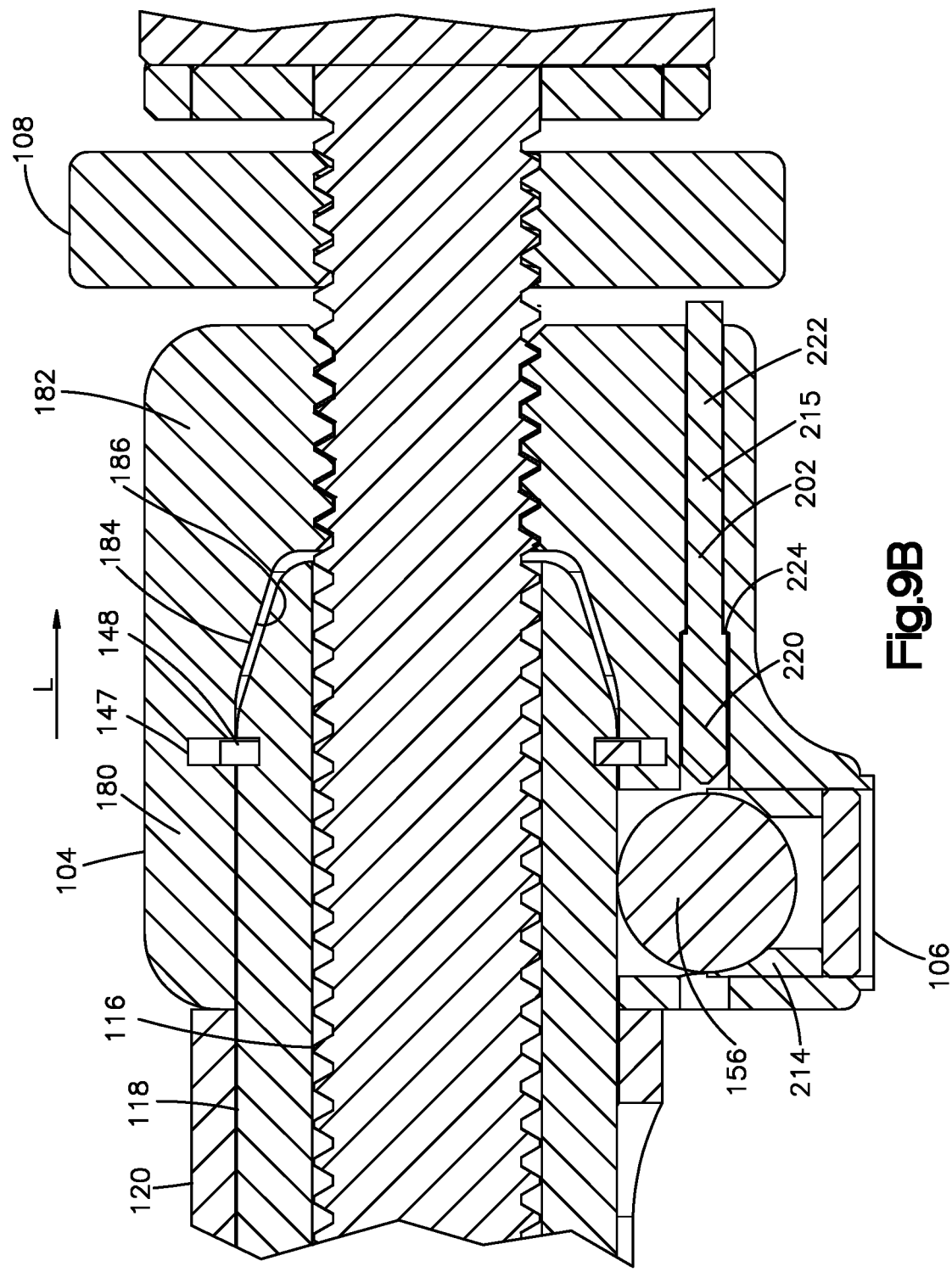
FIG. 9B illustrates a close-up view of a cross-section of the strut shown in FIG. 5 defined by the box A in a second configuration (e.g. unlocked configuration).

FIG. 9A illustrates a close-up view of a cross-section of the strut 24 defined by the box A shown in FIG. 5 when the locking assembly 106 is in a first configuration (e.g. locked configuration), and FIG. 9B illustrates a close-up view of a cross-section of the strut 24 defined by the box A shown in FIG. 5 when the locking assembly 106 is in a second configuration (e.g. unlocked configuration). The locking assembly 106 includes the lock member 156, the interference member 202, and a resilient member 214. The lock member 156 is configured to translate within the first lock channel 192 along the first lock axis $L_1$. The lock member 156 can comprise a ball member having a substantially spherical shape. It will be appreciated that the lock member 156 may comprise other configurations and/or shapes capable of translating within the first lock channel 192.

The lock member 156 can transition between a locked position (e.g. FIG. 9A) and an unlocked position (e.g. FIG. 9B). In the locked position, the lock member 156 is positioned at least partially within one of the plurality of detents 150 of the sleeve 118. When the lock member 156 is positioned within one of the plurality of detents 150, rotation between the sleeve 118 and the actuator 104 is substantially prevented. In the unlocked position, the lock member 156 is spaced apart from the sleeve 118 along the first lock axis $L_1$ and positioned externally from each of the plurality of detents 150. In the unlocked position, the sleeve 118 can rotate freely about the strut axis 72 relative to the actuator 104.

The resilient member 214 is configured to be received at least partially within the first lock channel 192. The resilient member 214 is positioned within the first lock channel 192 such that the lock member 156 is positioned between the resilient member 214 and the sleeve 118 along the first lock axis $L_1$. The resilient member 214 is configured to bias the lock member 156 into the locked position. The resilient member 214 can comprise a spring, or other component configured to provide a biasing force onto the lock member 156.

The interference member 202 is configured to translate within the second lock channel 198 along the second lock axis $L_2$. The configuration and shape of the interference member 202 can correspond to the configuration and shape of the second lock channel 198. For example, if the second lock channel 198 is substantially cylindrical, the interference member 202 can be substantially cylindrical. If the second lock channel 198 includes a rectangular shape, keyed portion, or other shape, the interference member 202 can have a corresponding rectangular shape, keyed portion, or other corresponding shape.

The interference member 202 can comprise a pin, rod, beam, or other component capable of extending through the second lock channel 198 from the first channel opening 204 to the second channel opening 206. The interference member 202 includes an elongate shaft 215 that extends from a first end 216 and a second end 218. The shaft 215 includes a first shaft portion 220 and a second shaft portion 222. The first shaft portion 220 extends along the second lock axis $L_2$ from the first end 216 to the second shaft portion 222. The second shaft portion 222 extends along the second lock axis $L_2$ from the first shaft portion 220 to the second end 218. The first shaft portion 220 can have a cross-sectional dimension that is greater than a cross-sectional dimension of the second shaft portion 222. A shaft shoulder 224 is defined between the first and second shaft portions 220 and 222. The shaft shoulder 224 can extend about the second lock axis $L_2$. The shaft shoulder 224 can abut against the channel shoulder 212 to affect movement of the interference member 202 positioned within the second lock channel 198.

The interference member 202 is configured to transition between a first interference position (e.g. FIG. 9A) and a second interference position (e.g. FIG. 9B). In the first interference position, the interference member 202 substantially prevents the lock member 156 from transitioning from the locked position to the unlocked position. The interference member 202 extends through the first channel opening 204 of the second lock channel 198, substantially preventing the lock member 156 from translating along the first lock axis $L_1$. In the second interference position, the lock member 156 is substantially free to transition between the locked position and the unlocked position. The interference member 202 transitions from the first interference position to the second interference position by translating along the second lock axis $L_2$ in a direction that extends from the first channel opening 204 to the second channel opening 206. The interference member 202 can translate along the second lock axis $L_2$ in the direction that extends from the first channel opening 204 to the second channel opening 206 until the shaft shoulder 224 abuts against or contacts the channel shoulder 212. The channel shoulder 212 prevents the interference member 202 from completely translating through the second lock channel 198.

The locking assembly 106 can also include a spacer member (not shown). The spacer member can be positioned between the resilient member 214 and the lock member 156 to limit or prevent contact between the interference member 202 and the resilient member 214 during use.

The nut lock member 108 (e.g. second lock member) is configured to be received on the threaded portion 124 of the rod 216. The nut lock member 108 can include an internal threaded portion that corresponds to the threaded portion 124. The nut lock member 108 is translatable relative to the actuator 104 along the strut axis 72 between a first nut position (e.g. retain position) and a second nut position (e.g. release position). In the first nut position, the nut lock member 108 substantially prevents the interference member 202 from transitioning from the first interference position to the second interference position. For example, the nut lock member 108 can abut against the second end 218 of the interference member 202, preventing the interference member from translating along the second lock axis $L_2$ in the direction that extends from the first channel opening 204 to the second channel opening 206. In an aspect, the nut lock member 108 abuts against the outer surface 196 of the actuator 104. In the second nut position, the interference member 202 is substantially free to transition between the first interference position and the second interference position. In an aspect, the nut lock member 108 is spaced apart from the outer surface 196 of the actuator 104 to allow the interference member 202 to translate along the second lock axis $L_2$.

The strut 24 can further include the first rotation assembly 138 and the second rotation assembly 140. The first rotation assembly 138 can be coupled to the rod 116 by the retention member 136, and the second rotation assembly 140 can be coupled to the housing member 120 by the retention member 176. The first rotation assembly 138 and the second rotation assembly 140 can be rotationally free (e.g. polyaxial joints) relative to the rod 116 and the housing member 120, respectively. The first rotation assembly 138 can include components that can prevent or control the rotation of the first end 112 of the strut 24 relative to the rod 116. Similarly, the second rotation assembly 140 can include components that can prevent or control the rotation of the second end 114 of the strut 24 relative to the housing member 120. It will be appreciated that the strut 24 can include other components including, for example, first and second joints (e.g. single axis joints) coupled to the first and second ends 112 and 114 of the strut 24. Alternatively, the first and second joints could replace the first and second rotation assemblies 138 and 140, and be coupled directly to the rod 116 and the housing member 120, respectively.

The strut 24 can also include one or more indication members configured to be supported by the strut body 102. Each indication member can include information that identifies or distinguishes each strut 24. In an aspect, the identification members can be color coded. The color coded identification members can facilitate, for example, the user completing a treatment plan.

During a procedure, the first end 112 of the strut 24 is attached to the first base 22a, and the second end 114 of the strut 24 is attached to the second base 22b. Multiple struts 24 can be attached between the first and second bases 22a and 22b, as described and illustrated above. The below description describes the movement and control of a single strut 24, however, it will be appreciated that the movement and control described below can apply to the multiple struts 24 attached between the first and second bases 22a and 22b.

After the strut 24 is coupled to the first and second bases 22a and 22b, the length $D_1$ can be controlled by rotating the actuator 104. For example, rotating the actuator 104 in a first rotational direction about the rod 116 causes the actuator 104 and the sleeve 118 to translate along the strut axis 72 toward the first end 126 of the rod 116, thereby reducing the length $D_1$ of the strut 24. Rotating the actuator 104 in a second rotational direction about the rod 116 opposite to the first rotational direction causes the actuator 104 and the sleeve 118 to translate along the strut axis 72 toward the second end 128 of the rod 116, thereby increasing the length $D_1$ of the strut 24.

With reference to FIGS. 9A and 9B, during rotation of the actuator 104, the lock member 156 rotates circumferentially about strut axis 72 relative to the sleeve 118. The lock member 156 can enter and exit one or more of the detents 150 of the sleeve 118 as the actuator 104 rotates. Each time the lock member 156 enters and/or exits one of the plurality of detents 150, the lock member 156 can provide a tactile feedback, an auditory feedback, or other feedback to indicate a change in rotational position of the actuator 104 relative to the sleeve 118. The feedback can provide an indication to the physician about how much the length $D_1$ has been modified during rotation of the actuator 104.

When adjusting the length $D_1$ of the strut 24, the actuator 104 rotates about the strut axis 72 relative to the sleeve 118. When a desired length $D_1$ is achieved, the strut 24 can be locked into position by actuating the locking assembly 106. The locking assembly 106 can be actuated by rotating the nut lock member 108 about the strut axis 72, causing the nut lock member 108 to translate along the strut axis 72 toward the actuator 104. While adjusting the length $D_1$, the nut lock member 108 is in the release position, such that the interference member 202 can translate along the second lock axis $L_2$, allowing the lock member 156 to translate along the first lock axis $L_1$. The length $D_1$ can be locked by transitioning the nut lock member 108 to the retain position (FIG. 9A), which locks the interference member 202 in the first interference position, which locks the lock member 156 in the locked position. When the lock member 156 is in the locked position, the actuator 104 is substantially prevented from rotating about the sleeve 118, thereby preventing the actuator 104 from rotating about the rod 116. Since the actuator 104 is prevented from rotating about the strut axis 72 relative to the rod 116, the length $D_1$ is substantially fixed.

To re-adjust the length $D_1$ of the strut 24, the nut lock member 108 can be transitioned to the release position (e.g. FIG. 9B) by rotating the nut lock member 108 about the strut axis 72 relative to the rod 116. Transitioning the nut lock member 108 to the release position allows the interference member 202 to transition to the second interference position, which allows the lock member 156 to transition to the unlocked position. When the nut lock member 108 is in the release position, the actuator 104 is free to rotate about the sleeve 118, which allows the actuator 104 to rotate about the rod 116 to adjust the length $D_1$.

The lock assembly 106 prevents the length $D_1$ from unintentional adjusting. For example, a conventional strut can be loosened by bumping or other inadvertent contact. If a strut becomes loose, the length $D_1$ can adjust and adversely impact the treatment of the patient. The locking assembly 106 provides the nut lock member 108 which can prevent linear movement of the actuator 104 along the strut axis, while also locking the actuator 104 to the sleeve 118, providing a second lock, or passive lock, that further prevents the unintentional adjustment.

The design of the strut 27, as disclosed herein allows the physician to utilize any of the foregoing modes of expansion and/or contraction to achieve the final desired configuration, and to adjust the configuration of the device 20 as necessary, including during subsequent physical procedures on the patient.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A strut assembly configured to be connected to a pair of external bone fixation members along a strut axis, the strut assembly comprising:
    a sleeve that includes a sleeve body and a sleeve bore that extends through the sleeve body along the strut axis, wherein the sleeve has an outer surface that defines a plurality of detents spaced circumferentially about the outer surface of the sleeve;
    a rod rotatably fixed with respect to the sleeve, the rod having a threaded outer surface, wherein the rod extends through the sleeve bore along the strut axis such that the rod is translatable relative to the sleeve along the strut axis;
    an actuator that includes an actuator body and an inner actuator surface that defines an actuator bore that extends through the actuator body along the strut axis, wherein the inner actuator surface is threadedly engaged with the threaded outer surface of the rod, such that rotation of the actuator about the strut axis relative to the rod causes the rod to translate relative to the actuator through the actuator bore and relative to the sleeve through the sleeve bore thereby adjusting a length between the bone fixation members along the strut axis, wherein the actuator defines first and second lock channels that extend at least partially therethrough;
    a lock member configured to transition between a locked position in which the lock member is locked to the sleeve and the actuator so as to prevent relative rotation between the actuator and the rod, and an unlocked position whereby the lock member does not prevent relative rotation between the actuator and the rod, wherein the first lock channel is configured to receive the lock member within,
    wherein when the lock member is in the unlocked position, 1) the lock member is spaced apart from the plurality of detents, and 2) a rotational force applied to the actuator is sufficient to cause the actuator to rotate about the rod, and when the lock member is in the locked position, 1) the lock member is positioned at least partially within both of the first lock channel and at least one of the plurality of detents, and 2) the lock member prevents the rotational force from causing the actuator to rotate about the rod; and
    an interference member that is configured to be received within the second lock channel, the interference member being configured to transition between a first interference position in which the interference member substantially prevents the lock member from transitioning from the locked position to the unlocked position, and a second interference position in which the lock member is substantially free to transition between the locked position and the unlocked position.

2. The strut assembly of claim 1, wherein the lock member comprises a ball member having a substantially spherical shape, and wherein each of the plurality of detents defines at least a partially hemispherical shape configured to receive the ball member within.

3. The strut assembly of claim 2, wherein when the ball member transitions from the unlocked position to the locked position the ball member provides at least one of a tactile feedback and an auditory feedback.

4. The strut assembly of claim 1, wherein the actuator includes a resilient member positioned at least partially within the lock channel, the resilient member being configured to bias the lock member into the locked position.

5. The strut assembly of claim 1, wherein the interference member includes an elongate shaft that extends from a first end to a second end, the elongate shaft including a first shaft portion and a second shaft portion, the first shaft portion extending from the first end of the shaft to the second shaft portion, and the second shaft portion extending from the first shaft portion to the second end of the shaft, wherein the first shaft portion has a cross sectional diameter that is greater than a cross sectional diameter of the second shaft portion defining a shaft shoulder between the first shaft portion and the second shaft portion, and
    wherein the second lock channel extends along a lock axis from a first channel opening to a second channel opening, the second lock channel including a first channel portion and a second channel portion, the first channel portion extending from the first channel opening to the second channel portion, and the second channel portion extending from the first channel portion to the second opening, wherein the first channel portion has a cross sectional dimension that is greater than a cross sectional dimension of the second channel portion defining a channel shoulder between the first channel portion and the second channel portion,
    wherein when the elongate shaft is positioned within the second lock channel the shaft is 1.) substantially free to move along the lock axis in a direction from the second opening toward the first opening, and 2.) substantially prevented from moving along the lock axis in a direction from the first opening to the second opening when the shaft shoulder engages the channel shoulder.

6. The strut assembly of claim 1, further comprising:
a nut lock member translatable relative to the actuator along the strut axis between a first nut position in which the nut lock member substantially prevents the interference member from transitioning from the first interference position to the second interference position, and a second nut position in which the interference member is substantially free to transition between the first interference position and the second interference position.

7. The strut assembly of claim 1, wherein when the lock member is in the unlocked position, the actuator is substantially free to rotate about the sleeve.

8. A strut assembly extending along a strut axis, the strut assembly comprising:
a sleeve that includes a sleeve body and a sleeve bore that extends through the sleeve body along the strut axis;
a rod rotatably fixed with respect to the sleeve, the rod having a threaded outer surface, wherein the rod extends through the sleeve bore along the strut axis such that the rod is translatable relative to the sleeve along the strut axis;
an actuator that includes an actuator body, an inner actuator surface that defines an actuator bore that extends through the actuator body along the strut axis, and a lock surface that defines a lock channel that extends at least partially through the actuator, wherein the inner actuator surface is threadedly engaged with the threaded outer surface of the rod, such that rotation of the actuator about the strut axis relative to the rod causes the rod to translate relative to the actuator through the actuator bore and relative to the sleeve through the sleeve bore thereby adjusting a length of the strut assembly along the strut axis;
a first lock member positioned at least partially within the lock channel of the actuator, the first lock member being configured to transition between a locked position in which the lock member engages both the sleeve and the actuator so as to prevent relative rotation between the actuator and the rod, and an unlocked position whereby the lock member does not prevent relative rotation between the actuator and the rod; and
a second lock member being threadedly engaged with the threaded outer surface of the rod such that rotation of the second lock member relative to the rod about the strut axis causes the second lock member to translate relative to the rod along the strut axis, the second lock member being configured to transition between a retain position in which the second lock member substantially prevents the first lock member from transitioning from the locked position to the unlocked position, and a release position in which the first lock member is substantially free to transition between the locked position and the unlocked position,
wherein the lock channel is a first lock channel, the actuator further defining a second lock channel, the strut assembly further comprising an interference member positioned within the second lock channel, the interference member extending between the first lock member and the second lock member, wherein in the retain position of the second lock member the interference member engages the first lock member substantially preventing the first lock member from transitioning from the lock position to the unlock position.

9. The strut assembly of claim 8, wherein the second lock channel extends from the first lock channel to an opening that opens to a location external to the actuator, wherein the interference member defines an interference shoulder on an outer surface, and wherein the second lock channel defines a channel shoulder on an inner surface, wherein the interference member is substantially prevented from moving in a direction from the first lock channel toward the opening when the interference shoulder engages the channel shoulder.

10. The strut assembly of claim 8, further comprising:
a resilient member positioned within the lock channel of the actuator, the resilient member being configured to bias the first lock member into the locked position.

11. The strut assembly of claim 8, wherein an outer surface of the sleeve defines at least one detent, wherein in the locked position of the first lock member the first lock member is positioned at least partially within both of the first lock channel and the at least one detent, and wherein in the unlocked position of the first lock member the first lock member is spaced apart from the at least one detent.

12. The strut assembly of claim 11, wherein the at least one detent comprises a plurality of detents spaced circumferentially about the outer surface of the sleeve.

13. The strut assembly of claim 12, wherein the lock member comprises a ball member having a substantially spherical shape, and wherein each of the plurality of detents defines at least a partially hemispherical shape configured to receive the ball member within.

14. The strut assembly of claim 13, wherein when the ball member transitions from the unlocked position to the locked position the ball member provides at least one of a tactile feedback and an auditory feedback.

\* \* \* \* \*